(12) United States Patent
Kohler Reidi et al.

(10) Patent No.: US 12,000,071 B2
(45) Date of Patent: Jun. 4, 2024

(54) METHOD OF MAKING A NONWOVEN FIBER WEB, NONWOVEN FIBER WEB, AND MULTI-COMPONENT FIBER

(71) Applicant: Solventum Intellectual Properties Company, Maplewood, MN (US)

(72) Inventors: Petra L. Kohler Reidi, Minneapolis, MN (US); Saurabh Batra, Minneapolis, MN (US); Hannah C. Cohen, St. Paul, MN (US); Semra Colak Atan, St. Louis Park, MN (US); Naimul Karim, Maplewood, MN (US); Joseph J. Stoffel, Hastings, MN (US); Joseph A. Dunbar, Woodbury, MN (US); Colby W. Dotseth, Baldwin, WI (US)

(73) Assignee: Solventum Intellectual Properties Company, Maplewood, MN (US)

( * ) Notice: Subject to any disclaimer, the term of this patent is extended or adjusted under 35 U.S.C. 154(b) by 128 days.

(21) Appl. No.: 17/595,549

(22) PCT Filed: Jun. 12, 2020

(86) PCT No.: PCT/IB2020/055550
§ 371 (c)(1),
(2) Date: Nov. 18, 2021

(87) PCT Pub. No.: WO2020/261035
PCT Pub. Date: Dec. 30, 2020

(65) Prior Publication Data
US 2022/0228306 A1    Jul. 21, 2022

Related U.S. Application Data

(60) Provisional application No. 62/866,664, filed on Jun. 26, 2019.

(51) Int. Cl.
*D04H 1/56* (2006.01)
*D01F 6/34* (2006.01)
(Continued)

(52) U.S. Cl.
CPC ............... *D04H 1/56* (2013.01); *D01F 6/34* (2013.01); *D01F 8/10* (2013.01); *D04H 1/4258* (2013.01);
(Continued)

(58) Field of Classification Search
None
See application file for complete search history.

(56) References Cited

U.S. PATENT DOCUMENTS 3,849,241 A    11/1974    Butin
4,118,531 A    10/1978    Hauser
(Continued)

FOREIGN PATENT DOCUMENTS

EP    1010783    6/2000
EP    3211046    8/2017
(Continued)

OTHER PUBLICATIONS

Jung, "Physical and Mechanical Properties of Plasticized Butenediol Vinyl Alcohol Copolymer/Thermoplastic Starch Blend", Journal of Vinyl and Additive Technology, May 2019, vol. 25, No. 2, pp. 109-116.
(Continued)

*Primary Examiner* — Shawn McKinnon

(57) ABSTRACT

A method of making a nonwoven fiber web comprises: providing a melt-blown nonwoven fiber web comprising bonded primary fibers having an average fiber diameter of 2 to 100 microns, wherein the primary fibers comprise a copolymer comprising divalent hydroxyethylene monomer units and divalent dihydroxybutylene monomer units; open-
(Continued)

ing at least a portion of the melt-blown nonwoven fiber web to provide loose primary fibers; combining the loose primary fibers with secondary fibers; and forming a secondary nonwoven fiber web comprising the primary fibers and secondary fibers. A fiber web preparable according to the method and a multicomponent fiber including a first phase comprising a copolymer comprising divalent hydroxyethylene monomer units and divalent dihydroxybutylene monomer units and a second phase comprising a non-biodegradable polymer.

5 Claims, 1 Drawing Sheet

(51) Int. Cl.
  *D01F 8/10* (2006.01)
  *D04H 1/4258* (2012.01)
  *D04H 1/4291* (2012.01)
  *D04H 1/4309* (2012.01)
(52) U.S. Cl.
  CPC ......... *D04H 1/4291* (2013.01); *D04H 1/4309* (2013.01)

(56) References Cited

U.S. PATENT DOCUMENTS

| | | |
|---|---|---|
| 4,215,682 A | 8/1980 | Kubik |
| 4,307,143 A | 12/1981 | Meitner |
| 4,707,398 A | 11/1987 | Boggs |
| 4,798,850 A | 1/1989 | Brown |
| 4,939,016 A * | 7/1990 | Radwanski ............... D04H 1/56 428/326 |
| 5,207,790 A | 5/1993 | Eveillard |
| 5,207,970 A | 5/1993 | Joseph |
| 5,232,770 A | 8/1993 | Joseph |
| 5,238,733 A | 8/1993 | Joseph |
| 5,258,220 A | 11/1993 | Joseph |
| 5,380,580 A | 1/1995 | Rogers |
| 5,401,446 A | 3/1995 | Tsai |
| 5,496,507 A | 3/1996 | Angadjivand |
| 5,698,322 A | 12/1997 | Tsai |
| 5,908,598 A | 6/1999 | Rousseau |
| 5,993,943 A | 11/1999 | Bodaghi |
| 6,119,691 A | 9/2000 | Angadjivand |
| 6,375,886 B1 | 4/2002 | Angadjivand |
| 6,397,458 B1 | 6/2002 | Jones |
| 6,406,657 B1 | 6/2002 | Eitzman |
| 6,454,986 B1 | 9/2002 | Eitzman |
| 6,494,974 B2 | 12/2002 | Riddell |
| 6,552,123 B1 | 4/2003 | Katayama et al. |
| 6,743,464 B1 | 6/2004 | Insley |
| 6,872,311 B2 | 3/2005 | Koslow |
| 7,008,207 B2 | 3/2006 | Bansal |
| 7,989,371 B2 | 8/2011 | Angadjivand |
| 8,026,302 B2 | 9/2011 | Shibutani |
| 8,404,171 B2 | 3/2013 | Heenan |
| 8,569,414 B2 | 10/2013 | Shibutani |
| 8,722,782 B2 | 5/2014 | Shibutani |
| 8,926,877 B2 | 1/2015 | Melik |
| 9,109,104 B2 | 8/2015 | Shibutani |
| 9,532,578 B2 | 1/2017 | Siddiqui |
| 9,765,166 B2 | 9/2017 | Shibutani |
| 10,315,749 B1 | 6/2019 | Walker et al. |
| 2003/0148690 A1 | 8/2003 | Bond et al. |
| 2005/0266760 A1 | 12/2005 | Chhabra |
| 2005/0287891 A1 | 12/2005 | Park |
| 2006/0096911 A1 | 5/2006 | Brey |
| 2008/0038976 A1 | 2/2008 | Berrigan |
| 2009/0061719 A1 | 3/2009 | Shibutani |
| 2009/0286909 A1 | 11/2009 | Shibutani et al. |
| 2009/0305592 A1 | 12/2009 | Shi et al. |
| 2011/0247839 A1 | 10/2011 | Lalouch |
| 2013/0108831 A1 | 5/2013 | Wu et al. |
| 2014/0030536 A1 | 6/2014 | Krishnaswamy |
| 2014/0374106 A1 | 12/2014 | Zhu |
| 2016/0235601 A1 | 8/2016 | Zhou et al. |
| 2016/0235608 A1 | 8/2016 | Zhuang et al. |
| 2017/0051442 A1 | 2/2017 | Endle |
| 2017/0191197 A1 | 7/2017 | Talwar |
| 2018/0290440 A1 | 10/2018 | Boswell |
| 2018/0291162 A1 | 10/2018 | Boswell |

FOREIGN PATENT DOCUMENTS

| | | | |
|---|---|---|---|
| WO | WO 2008-093615 | | 8/2008 |
| WO | 2009088648 A1 | | 7/2009 |
| WO | WO 2013-101702 | | 7/2013 |
| WO | WO2013101702 | * | 7/2013 |
| WO | WO 2016-109194 | | 7/2016 |
| WO | WO 2018-098803 | | 6/2018 |
| WO | WO 2019-027866 | | 2/2019 |

OTHER PUBLICATIONS

Wente, "Superfine Thermoplastic Fibers", Industrial & Engineering Chemistry, Aug. 1956, vol. 48, No. 8, pp. 1342-1346.
Wente, "Manufacture of Super Fine Organic Fibers," Report No. 4364 of the Naval Research Laboratories, May 1954, 19 pages.
International Search Report for PCT International Application No. PCT/IB2020/055550, dated Oct. 26, 2020, 6 pages.

* cited by examiner

METHOD OF MAKING A NONWOVEN FIBER WEB, NONWOVEN FIBER WEB, AND MULTI-COMPONENT FIBER

CROSS-REFERENCE TO RELATED APPLICATIONS

This application is a national stage filing under 35 U.S.C. 371 of PCT/IB2020/055550, filed Jun. 12, 2020, which claims the benefit of U.S. Provisional Application Ser. No. 62/866,664, filed Jun. 26, 2019, the disclosure of which is incorporated by reference in its entirety herein.

TECHNICAL FIELD

The present disclosure broadly relates to fibers and nonwoven fiber webs including them.

BACKGROUND

Highly hydrophilic, absorbent, and soluble fibers are useful as components in wound dressing materials. The most common materials used in these products are alginate and carboxymethyl cellulose. Many wound care products utilize cationic antiseptics, which kill a wide variety of microorganisms, but which are sequestered and/or deactivated by anionic materials such as alginate and carboxymethyl cellulose. Rayon is also a highly hydrophilic material used often in wound care products, but it also binds cationic antimicrobial molecules.

Melt-blowing is a process for forming nonwoven fiber webs of thermoplastic multi-component fibers. In a typical melt-blowing process, one or more thermoplastic (co)polymer streams are extruded through a die containing closely arranged orifices and attenuated by convergent streams of high-velocity hot air to form microfibers which are collected to form a melt-blown nonwoven fiber web. Multi-component melt-blown fibers and various apparatus and methods for making such fibers are also known. Thermoplastic (co)polymers commonly used in forming conventional melt-blown nonwoven fiber webs include polyethylene (PE) and polypropylene (PP). Melt-blown nonwoven fiber webs are used in a variety of applications, including acoustic and thermal insulation, filtration media, surgical drapes, and wipes, among others.

SUMMARY

In view of the art, it would be desirable to have fibers and nonwoven fiber webs that are useful for wound care products (e.g., bandages) that avoid the foregoing problems. The present disclosure provides non-ionic fiber materials suitable for use in wound dressings that avoid deactivation of cationic antiseptics. Additionally, these fiber materials may be non-toxic to human cells.

In a first aspect, the present disclosure provides a method of making a nonwoven fiber web, the method comprising:
a) providing a melt-blown nonwoven fiber web comprising bonded primary fibers having an average fiber diameter of 2 to 100 microns, wherein the primary fibers comprise a copolymer comprising divalent hydroxyethylene monomer units and divalent dihydroxybutylene monomer units;
b) opening at least a portion of the melt-blown nonwoven fiber web to provide loose primary fibers;
c) combining the loose primary fibers with secondary fibers; and
d) forming a secondary nonwoven fiber web comprising the primary fibers and secondary fibers.

In a second aspect, the present disclosure provides a secondary nonwoven fiber web made by a method according to the present disclosure.

In a third aspect, the present disclosure provides a nonwoven fiber web comprising a blend of at least primary fibers and secondary fibers, wherein the primary fibers comprise primary fibers having an average fiber diameter of 2 to 100 microns, and wherein the primary fibers comprise a copolymer comprising divalent hydroxyethylene monomer units and divalent dihydroxybutylene monomer units.

In a fourth aspect, the present disclosure provides a multi-component fiber comprising a first phase comprising a copolymer comprising divalent hydroxyethylene monomer units and divalent dihydroxybutylene monomer units and a second phase comprising a non-biodegradable polymer.

As used herein:
the term "monomer unit" refers to a residue in a polymer chain corresponding to a monomer, or basic salt (e.g., a conjugate base salt) of a monomer, used to form the polymer chain;
the term "fiber" can refer to a fiber of finite length or a filament of infinite length;
the term "nonwoven web" means a structure or a web of material which has been formed without use of weaving or knitting processes to produce a structure of individual fibers or threads which are intermeshed, but not in an identifiable, repeating manner. NOIMOVell webs have been, in the past, formed by a variety of conventional processes such as, for example, melt-blown processes and staple fiber carding processes.

Features and advantages of the present disclosure will be further understood upon consideration of the detailed description as well as the appended claims.

Figure 1:
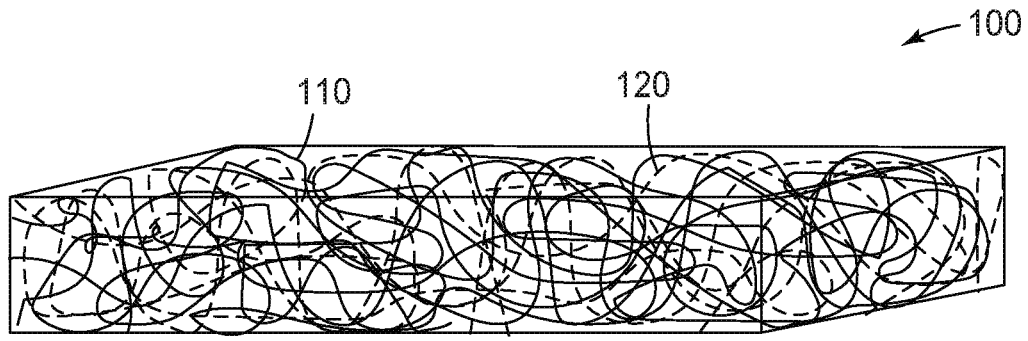
FIG. 1 is a schematic perspective view of a nonwoven fiber web 100 according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Referring now to FIG. 1, exemplary nonwoven fiber web 100 comprises primary fibers 110 and secondary fibers 120. Primary fibers 110 have an average fiber diameter of 2 to 100 microns and comprise a copolymer comprising divalent hydroxyethylene monomer units and divalent dihydroxybutylene monomer units.

The copolymer comprises divalent hydroxyethylene monomeric units

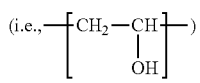

and divalent dihydroxybutylene monomer units. In preferred embodiments, the divalent dihydroxybutylene monomer units comprise 3,4-dihydroxybutan-1,2-diyl monomer units

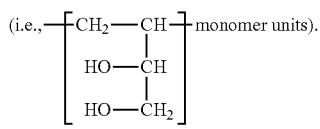

Optionally, but typically, the copolymer furthers comprise acetoxyethylene divalent monomeric units

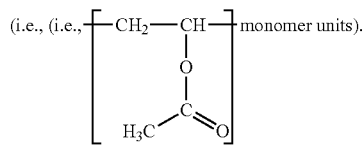

The copolymer may be obtained by copolymerization of vinyl acetate and 3,4-dihydroxy-1-butene followed by partial or complete saponification of the acetoxy groups to form hydroxyl groups. Alternatively, in place of 3,4-dihydroxy-1-butene, a carbonate such as

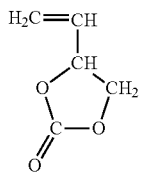

can also be used. After copolymerization, this carbonate may be hydrolyzed simultaneously with saponification of the acetate groups. In another embodiment, in place of 3,4-dihydroxy-1-butene, an acetal or ketal having the formula:

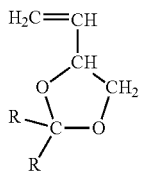

where each R is independently hydrogen or alkyl (e.g., methyl or ethyl). After copolymerization, this carbonate may be hydrolyzed simultaneously with saponification of the acetate groups, or separately. The copolymer can be made according to known methods or obtained from a commercial supplier, for example.

Commercially available copolymers may include those available under the trade designation Nichigo G-Polymer (Nippon Gohsei Synthetic Chemical Industry, Osaka, Japan), a highly amorphous polyvinyl alcohol, that is believed to have divalent monomer units of hydroxyethylene, 3,4-dihydroxybutan-1,2-diyl, and optionally acetoxyethylene. Nippon Gohsei also refers to Nichigo G-Polymer by the chemical name butenediol vinyl alcohol (BVOH). Exemplary materials include Nichigo G-Polymer grades AZF8035W, OKS-1024, OKS-8041, OKS-8089, OKS-8118, OKS-6026, OKS-1011, OKS-8049, OKS-1028, OKS-1027, OKS-1109, OKS-1081, and OKS-1083. These copolymers are believed to have a saponification degree of 80 to 97.9 mole percent, and further contain an alkylene oxide adduct of a polyvalent alcohol containing 5 to 9 moles of an alkylene oxide per mole of the polyvalent alcohol.

Melt-blowing methods are well-known in the art. As used herein, the term "melt-blown" refers to a process in which fibers are formed by extruding a molten thermoplastic material through a plurality of fine, usually circular, die capillaries into a high velocity gas (e.g., air) stream which attenuates the molten thermoplastic material and forms fibers, which can be to microfiber diameter, such as less than 10 microns in diameter. Thereafter, the melt-blown fibers are carried by the gas stream and are deposited on a collecting surface to form a web of random melt-blown fibers. Such a process is disclosed, for example, in U.S. Pat. Nos. 3,849,241 (Butin, et al.); 4,307,143 (Meitner, et al.); and 4,707,398 (Wisneski, et al.). Advantageously and unexpectedly, at least for the G-polymer materials, the inter-fiber bonding strength of the primary fibers in the melt-blown fiber web is sufficiently low that the web can be mechanically opened up to provide the individual primary fibers.

Primary fibers in accordance with the present disclosure may have circular and/or non-circular cross sections. Likewise, they may be continuous or discontinuous (e.g., random fiber or staple fiber). The average diameter of the primary fiber is 2 to 100 microns, preferably 3 to 60, more preferably 5 to 20 microns.

Melt-blown fiber webs made according to the present disclosure may have any basis weight and thickness for example, from 1 g/m$^2$ (gsm) to 400 gsm, 1 gsm to 200 gsm, 10 gsm to 200 gsm, 50 gsm to about 200 gsm, or even 100 gsm to about 200 gsm.

Optionally, the melt-blowing process may further comprise at least one of addition of a plurality of staple fibers to the plurality of discrete, discontinuous, multi-component fibers, or addition of a plurality of particulates to the plurality of discrete, discontinuous, multi-component fibers, to form a composite nonwoven fiber web.

In some embodiments, a substantially uniform distribution of particles throughout the web is desired. There may also be instances where non-uniform distributions may be advantageous. In certain exemplary embodiments, a particulate density gradient may advantageously be created within the composite nonwoven fiber web. For example, gradients through the depth of the web may create changes to the pore size distribution that could be used for depth filtration. Webs with a surface loading of particles could be formed into a filter where the fluid is exposed to the particles early in the flow path and the balance of the web provides a support structure and means to prevent sloughing of the particles. The flow path could also be reversed so the web can act as a pre-filter to remove some contaminants prior to the fluid reaching the active surface of the particles. Various methods are known for adding a stream of particulates to a nonwoven fiber stream. Suitable methods are described in U.S. Pat. Nos. 4,118,531 (Hauser), 6,872,3115 (Koslow), and 6,494,974 (Riddell); and in U.S. Pat. Appl. Publ. Nos. 2005/0266760 (Chhabra and Isele), 2005/0287891 (Park) and 2006/0096911 (Brey et al.). In other exemplary embodiments, the optional particulates may be added to a nonwoven fiber stream by air laying a fiber web, adding particulates to the fiber web (e.g., by passing the web through a fluidized bed of particulates), optionally with post heating of the particulate-loaded web to bond the particulates to the fibers.

Alternatively, a pre-formed nonwoven fiber web could be sprayed with a preformed dispersion of particulates in a volatile fluid (e.g., an organic solvent, or even water), optionally with post heating of the particulate-loaded web to remove the volatile fluid and bond the particulates to the fibers. In further exemplary embodiments, the process further includes collecting the plurality of discrete, discontinuous, multi-component fibers as the nonwoven fiber web on a collector. In certain such exemplary embodiments, a composite nonwoven fiber web may be formed by depositing the population of fine, ultrafine or sub-micrometer fibers directly onto a collector surface, or onto an optional support layer on the collector surface, the support layer optionally comprising microfibers, so as to form a population of fine, ultrafine or sub-micrometer fibers on the porous support layer.

The process of making a melt-blown fiber web may include a step wherein the optional support layer, which optionally may comprise polymeric microfibers, is passed through a fiber stream of fine, ultrafine or sub-micrometer fibers. While passing through the fiber stream, fine, ultrafine or sub-micrometer fibers may be deposited onto the support layer so as to be temporarily or permanently bonded to the support layer. When the fibers are deposited onto the support layer, the fibers may optionally bond to one another, and may further harden while on the support layer. In certain exemplary embodiments, the fine, ultrafine or sub-micrometer fiber population is combined with an optional porous support layer that comprises at least a portion of the coarse microfiber population. In some exemplary embodiments, the microfibers forming the porous support layer are compositionally the same as the population of microfibers that forms the first layer. In other presently preferred embodiments, the fine, ultrafine or sub-micrometer fiber population is combined with an optional porous support layer and subsequently combined with at least a portion of the coarse microfiber population. In some embodiments, the porous support layer adjoins the second layer opposite the first layer. In other exemplary embodiments, the porous support layer comprises a nonwoven fabric, a woven fabric, a knitted fabric, a foam layer, a screen, a porous film, a perforated film, an array of filaments, or a combination thereof In some exemplary embodiments, the porous support layer comprises a thermoplastic mesh.

In some embodiments, the melt-blown fiber web making process further includes processing the collected nonwoven fiber web using a process selected from autogenous bonding (e.g., through-air bonding and/or calendering), electret charging, embossing, needletacking, or a combination thereof Depending on the condition of the fibers and the relative proportion of microfibers and sub-micrometer fibers, some bonding may occur between the fibers themselves (e.g., autogenous bonding) and between the fibers and any optional particulates, before or during collection. However, further bonding between the fibers themselves and between the fibers and any optional particulates in the collected web may be desirable to provide a matrix of desired coherency, making the web more handleable and better able to hold any sub-micrometer fibers within the matrix ("bonding" fibers themselves means adhering the fibers together firmly, so they generally do not separate when the web is subjected to normal handling).

In certain exemplary embodiments, a blend of microfibers and sub-micrometer fibers may be bonded together. Bonding may be achieved, for example, using thermal bonding, adhesive bonding, powdered binder, needletacking, calendering, or a combination thereof. Conventional bonding techniques using heat and pressure applied in a point-bonding process or by smooth calender rolls can be used, though such processes may cause undesired deformation of fibers or excessive compaction of the web. A presently preferred technique for bonding fibers, particularly microfibers, is the autogenous bonding method disclosed in U.S. Pat. Appl. Publ. No. 2008/0038976 A1 (Berrigan et al.).

In some embodiments, the melt-blown fibers may be advantageously electrostatically charged. Thus, in certain exemplary embodiments, the melt-blown fibers may be subjected to an electret charging process. An exemplary electret charging process is hydrocharging. Hydrocharging of fibers may be carried out using a variety of techniques including impinging, soaking or condensing a polar fluid onto the fiber, followed by drying, so that the fiber becomes charged. Representative patents describing hydro-charging include U.S. Pat. Nos. 5,496,507 (Angadjivand et al.); 5,908,598 (Rousseau et al.); 6,375,886 (Angadjivand et al.); 6,406,657 B1 (Eitzman et al.); 6,454,986 (Eitzman et al.), and 6,743,464 B1 (Insley et al.).

Devices useful for hydraulically entangling fibers are generally useful for carrying out hydro-charging, although the operation is carried out at lower pressures in hydro-charging than generally used in hydro-entangling. U.S. Pat. No. 5,496,507 (Angadjivand et al.) describes an exemplary apparatus in which jets of water or a stream of water droplets are impinged upon the fibers in web form at a pressure sufficient to provide the subsequently-dried media with a filtration-enhancing electret charge.

The pressure necessary to achieve optimum results may vary depending on the type of sprayer used, the type of (co)polymer from which the fiber is formed, the thickness and density of the web, and whether pretreatment such as corona charging was carried out before hydro-charging. Generally, pressures in the range of about 69 kPa to about 3450 kPa are suitable. Preferably, the water used to provide the water droplets is relatively pure. Distilled or deionized water is preferable to tap water.

Fibers (e.g., in nonwoven fiber webs) may be subjected to other charging techniques in addition to or alternatively to hydro-charging, including electrostatic charging (e.g., as described in U.S. Pat. Nos. 4,215,682 (Kubik et al.), 5,401,446 (Tsai et al.) and 6,119,691 (Angadjivand et al.)), tribo-charging (e.g., as described in U.S. Pat. No. 4,798,850 (Brown)) or plasma fluorination (e.g., as described in U.S. Pat. No. 6,397,458 B1 (Jones et al.)). Corona charging followed by hydro-charging and plasma fluorination followed by hydrocharging are particularly suitable charging techniques used in combination.

Various processes conventionally used as adjuncts to fiber-forming processes may be used in connection with fibers as they exit from one or more orifices of the belt blowing die. Such processes include spraying of finishes, adhesives or other materials onto the fibers, application of an electrostatic charge to the fibers, application of water mists to the fibers, and the like. In addition, various materials may be added to a collected web, including bonding agents, adhesives, finishes, and other webs or films. For example, prior to collection, extruded fibers or fibers may be subjected to a number of additional processing steps, e.g., further drawing, spraying, and the like. Various fluids may also be advantageously applied to the fibers before or during collection, including water sprayed onto the fibers, e.g., heated water or steam to heat the fibers, or cold water to quench the fibers.

After collection, the collected mass may additionally or alternatively be wound into a storage roll for later processing if desired. Generally, once the collected melt-blown nonwoven fiber web has been collected, it may be conveyed to other apparatus such as a calender, embossing stations, laminators, cutters and the like; or it may be passed through drive rolls and wound into a storage roll.

Loose primary fibers may be combined with the secondary fibers in any suitable method to achieve the secondary fiber web. Such methods are well known in the nonwoven fiber web art. For example, the primary and secondary fibers can be mechanically and/or air mixed to form a nonwoven fiber web.

Nonwoven fiber webs may be made, for example, by conventional air laid, carded, stitch bonded, spun bonded, wet laid, and/or melt blown procedures. In some embodiments, a nonwoven web may be made by air-laying of fibers. Air-laid nonwoven fiber webs may be prepared using equipment such as, for example, that available as a RANDO WEBBER from Rando Machine Company of Macedon, New York. In some embodiments, a type of air-laying may be used that is termed gravity-laying, as described e.g., in U.S. Pat. Application Publication 2011/0247839 to Lalouch, the disclosure of which is incorporated by reference herein.

Nonwoven fiber webs may be densified and strengthened, for example, by techniques such as crosslapping, stitchbonding, needletacking, chemical bonding, and/or thermal bonding.

Exemplary suitable secondary fibers may be continuous or staple. The secondary fibers can be uncrimped or crimped, random, and/or chopped. The secondary fibers may have a fiber diameter up to about 500 microns, for example from 0.5 denier to 100 denier, from 0.5 denier to 50 denier, from 0.5 denier to 25 denier, from 0.5 denier to about 15 denier, or even from 0.5 denier to about 10 denier for polymeric or natural fibers. Useful secondary fibers may be natural, synthetic, inorganic (fiberglass, metallic and ceramic fibers), or a combination thereof.

As used herein, the term "denier" refers to an international unit indicating the thickness of the fiber yarn and the like, which means the weight in g of a fiber having a length of 9000 meters. When the denier of a fiber is less than 3, the fiber may be easily broken so that it is difficult to manufacture and handle a nonwoven fiber web. Herein, the basis weight means the weight (g) of the nonwoven web 1 per unit area (sqm).

Exemplary synthetic fibers may comprise at least one of polyolefin (e.g., polyethylene (HDPE, LDPE, LLDPE, VLDPE; ULDPE, UHMW-PE), polypropylene, poly(1-butene), polyisobutylene, poly(1-pentene), poly(4-methyl-pent-1-ene), polybutadiene, polyisoprene, styrenic block copolymers (e.g., styrene-isoprene-styrene (SIS) block copolymers, styrene-ethylene-butadiene-styrene (SEBS) block copolymers, or styrene-butadiene-styrene (SBS) block copolymers)) fibers, polyester (e.g., polylactic acid, polyethylene terephthalate, polytrimethylene terephthalate , polycaprolactone, polyethylene naphthalate, polylactic acid, polybutylene terephthalate) fibers, polyamide (e.g., polycaprolactam or nylon 6,6) fibers, acrylic (e.g., acrylonitrile) fibers, polyvinyl alcohol fibers, polycarbonate fibers, polystyrene fibers, polyphenylene sulfide fibers, polysulfone fibers polyoxymethylene fibers, polyimide fibers, polyurea fibers, rayon fibers, or polyurethane fibers.

Exemplary suitable natural fibers include cotton fibers, wool fibers, cashmere fibers, kenaf fibers, jute fibers, flax fibers, hemp fibers, cellulosic fibers, sisal fibers, coir fibers, and combinations thereof.

Exemplary suitable metallic fibers include stainless steel fibers, nickel fibers, titanium fibers, copper fibers, aluminum fibers, and combinations thereof.

Nonwoven fiber webs according to the present disclosure may have any basis weight, thickness, porosity, and/or density unless otherwise specified. In some embodiments, the nonwoven fiber webs are lofty open nonwoven fiber webs.

In addition to the foregoing methods of making and optionally bonding or electret charging a nonwoven fiber web, one or more of the following process steps may optionally be carried out once the nonwoven fiber web is formed:

(1) advancing the nonwoven fiber web along a process pathway toward further processing operations;
(2) bringing one or more additional layers into contact with an outer surface of the sub micrometer fiber component, the microfiber component, and/or the optional support layer;
(3) calendering the nonwoven fiber web;
(4) coating the nonwoven fiber web with a surface treatment or other composition (e.g., a fire-retardant composition, an adhesive composition, or a print layer);
(5) attaching the nonwoven fiber web to a cardboard or plastic tube;
(6) winding-up the nonwoven fiber web in the form of a roll;
(7) slitting the nonwoven fiber web to form two or more slit rolls and/or a plurality of slit sheets;
(8) placing the nonwoven fiber web in a mold and molding the nonwoven fiber web into a new shape; and
(9) applying a release liner over an exposed optional pressure-sensitive adhesive layer, when present.

While fiber blends of primary and secondary fibers are useful for making nonwoven fiber webs as discussed above, if the primary and second fiber materials are extrudable it is also possible to combining the primary and secondary fiber materials within a single multi-component fiber. Nonwoven fiber webs made from these multi-component fibers may have similar or superior properties as compared to nonwoven fiber blend webs of the same polymers.

Figure 2:
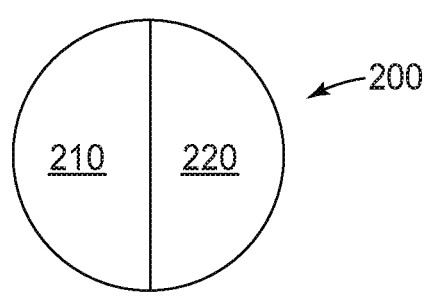
FIG. 2 is a schematic cross-sectional view of a multi-component fiber 200 according to one embodiment of the present disclosure.

Referring now to FIG. 2, exemplary multi-component fiber 200 comprises a first phase 210 and a second phase 220. First phase 210 comprises a copolymer comprising divalent hydroxyethylene monomer units and divalent dihydroxybutylene monomer units as described hereinabove. Second phase 220 comprises a non-biodegradable polymer. Either of both of the first and second phases may be continuous of discontinuous.

While the multi-component fiber 200 shown in FIG. 2 has a circular cross-section, other cross-sections may also be used such as, for example, triangular, square, rectangular, pentagonal, hexagonal, heptagonal, octagonal, star-shaped, oval, trilobal, and tetralobal.

Figure 3A:
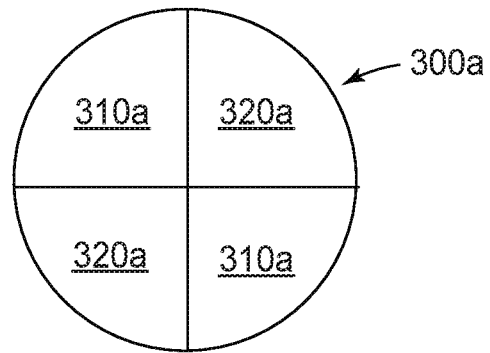
FIGS. 3A-3C are schematic cross-sectional views of a multi-component fibers 300a-c according to various embodiments of the present disclosure.
Figure 3B:
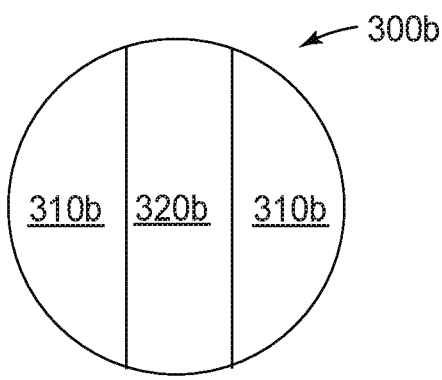
Figure 3C:
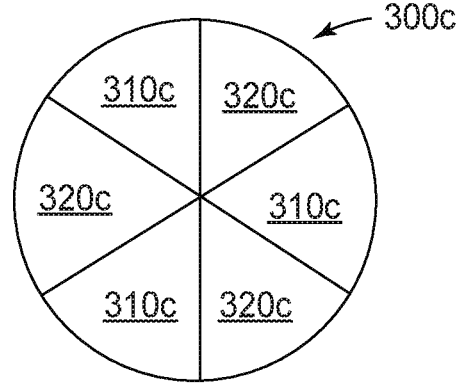

FIGS. 3A-3C show various other exemplary configurations of the first and second phases (310a-c, 320a-c) within the multi-component fiber 300a-c. Other configurations not shown may also be used. For example, a core-sheath construction wherein BVOH polymer is included in the sheath and a non-biodegradable polymer is included in the fiber core may be desirable in some circumstances.

Multi-component fibers can be made by well-known coextrusion techniques. For example, details concerning multi-component fiber manufacturing extrusion techniques can be found in U.S. Pat. Nos. 5,207,790 and 5,232,770 (Joseph et al.), the disclosures of which are incorporated herein by reference.

Non-biodegradable polymers are those polymers that are not decomposed under aerobic or anaerobic conditions as a result of the action of microorganisms/enzymes.

Non-biodegradable polymers include polyolefins such as polyethylenes (e.g., HDPE, LDPE, LLDPE, VLDPE; ULDPE, UHMW-PE grades), polypropylenes, polybutylenes, poly(ether ether ketone), and poly-4-methylpentenes), certain polyesters (e.g., polyethylene terephthalate), polyvinyl chloride, certain acrylic polymers (e.g., polymethyl methacrylate, polyacrylonitrile), certain polyamides, polystyrene, styrenic block copolymers (e.g., SIS, SEBS, SBS), polysulfones, and certain polyurethanes.

The multi-component fiber may have any fiber diameter, the average diameter is 2 to 100 microns, preferably 3 to 60 microns, more preferably 5 to 20 microns, and may be continuous, random, or staple fiber. The multi-component fiber may be crimped on non-crimped.

Methods for making multi-component fibers are well known and need not be described here in detail. To form a multi-component fiber, generally, feeding the first and second molten mixtures as separate liquid streams to at least one orifice to form at least one multi-component molten filament comprised of the first (co)polymeric component and the second (co)polymeric component applying a gaseous stream to the at least one multi-component molten filament to attenuate the at least one multi-component molten filament to form a plurality of discrete, discontinuous multi-component fibers; and cooling the plurality of discrete, discontinuous, multi-component fibers to a temperature below the melting temperature of the first (co)polymeric component mixture and the melting temperature of the second (co)polymeric component to solidify the discrete, discontinuous, multi-component fibers and thereby form a nonwoven fiber web.

In some exemplary embodiments, the discrete, discontinuous, multi-component fibers exhibit an axial cross-sectional structure selected from the group consisting of a plurality of alternating layers of the first (co)polymeric component and the second (co)polymeric component, a plurality of alternating pie wedges of the first (co)polymeric component and the second (co)polymeric component, and a core/sheath structure wherein the first (co)polymeric component makes up substantially all of the sheath.

In some exemplary embodiments, applying a gaseous stream to at least one filament to attenuate the at least one filament to form a plurality of discrete, discontinuous, multi-component fibers is accomplished using a process selected from melt-blowing, gas jet fibrillation, and combinations thereof. In some such exemplary embodiments, the process further includes at least one of addition of a plurality of staple fibers to the plurality of discrete, discontinuous, multi-component fibers, or addition of a plurality of particulates to the plurality of discrete, discontinuous, multi-component fibers.

In further such exemplary embodiments, the process further includes collecting the plurality of discrete, discontinuous, multi-component fibers as the nonwoven fiber web on a collector. In some such embodiments, the process further includes processing the collected nonwoven fiber web using a process selected from autogenous bonding, through-air bonding, electret charging, embossing, needle-punching, needle tacking, or a combination thereof.

A number of processes may be used for producing discrete multi-component fibers. Suitable processes and apparatus for producing discrete multi-component fibers include those described in U.S. Pat. Nos. 5,698,322 (Tsai et al), 7,008,207 B2 (Bansal et al.), and 8,926,877 B2 (Melik et al.). Particularly useful apparatus and methods, more particularly feed blocks for feeding multiple molten polymer streams to the die orifice(s) for producing discrete multi-component melt-blown fibers, are disclosed in U.S. Pat. Nos. 5,207,970 (Joseph et al.); 5,258,220 (Joseph et al.); 5,238,733 (Joseph et al.); and 5,232,770 (Joseph et al.), each incorporated herein by reference in its entirety.

Multi-component fibers and nonwoven fiber webs according to the present disclosure may be included in personal hygiene products, wound care products (e.g., bandages), filtration media, etc.

SELECT EMBODIMENTS OF THE PRESENT DISCLOSURE

In a first embodiment, the present disclosure provides a method of making a nonwoven fiber web, the method comprising:
 a) providing a melt-blown nonwoven fiber web comprising bonded primary fibers having an average fiber diameter of 2 to 100 microns, wherein the primary fibers comprise a copolymer comprising divalent hydroxyethylene monomer units and divalent dihydroxybutylene monomer units;
 b) opening at least a portion of the melt-blown nonwoven fiber web to provide loose primary fibers;
 c) combining the loose primary fibers with secondary fibers; and
 d) forming a secondary nonwoven fiber web comprising the primary fibers and secondary fibers.

In a second embodiment, the present disclosure provides a method according to the first embodiment, wherein the copolymer further comprises divalent acetoxyethylene monomer units.

In a third embodiment, the present disclosure provides a method according to the first or second embodiment, wherein the divalent dihydroxybutylene monomer units comprise divalent 3,4-dihydroxybutan-1,2-diyl monomer units.

In a fourth embodiment, the present disclosure provides a method according to any of the first to third embodiments, wherein the secondary fibers comprise at least one of polyolefin fibers, polyester fibers, polyamide fibers, styrenic block copolymer fibers, polyurethane fibers, metal fibers, ceramic fibers, or natural fibers.

In a fifth embodiment, the present disclosure provides a method according to any of the first to fourth embodiments, wherein said forming the secondary nonwoven fiber web comprises airlaying a fiber blend comprising the loose primary fibers and the secondary fibers.

In a sixth embodiment, the present disclosure provides a secondary nonwoven fiber web made according to any of the first to fifth embodiments.

In a seventh embodiment, the present disclosure provides a nonwoven fiber web comprising a blend of at least primary fibers and secondary fibers, wherein the primary fibers comprise primary fibers having an average fiber diameter of 2 to 100 microns, and wherein the primary fibers comprise a copolymer comprising divalent hydroxyethylene monomer units and divalent dihydroxybutylene monomer units.

In an eighth embodiment, the present disclosure provides a nonwoven fiber web according to the seventh embodiment, wherein the secondary fibers comprise at least one of polyolefin fibers, polyester fibers, polyamide fibers, polyurethane fibers, or natural fibers.

In a ninth embodiment, the present disclosure provides a nonwoven fiber web according to the eighth embodiment, wherein the polyolefin is selected from the group consisting of polyethylenes, polypropylenes, polybutylenes, styrenic block copolymers, and poly-4-methylpentenes.

In a tenth embodiment, the present disclosure provides a multi-component fiber comprising a first phase comprising a copolymer comprising divalent hydroxyethylene monomer units and divalent dihydroxybutylene monomer units and a second phase comprising a non-biodegradable polymer.

In an eleventh embodiment, the present disclosure provides a multi-component fiber according to the tenth embodiment, wherein the copolymer further comprises divalent acetoxyethylene monomer units.

In a twelfth embodiment, the present disclosure provides a multi-component fiber according to the tenth or eleventh embodiment, wherein the divalent dihydroxybutylene monomer units comprise divalent 3,4-dihydroxybutan-1,2-diyl monomer units.

In a thirteenth embodiment, the present disclosure provides a multi-component fiber according to any of the tenth to twelfth embodiments, wherein the non-biodegradable polymer comprises at least one of a polyolefin, a polyester, a polyamide, or a polyurethane.

In a fourteenth embodiment, the present disclosure provides a multi-component fiber according to the thirteenth embodiment, wherein the polyolefin is selected from the group consisting of polyethylenes, polypropylenes, polybutylenes, styrenic block copolymers, and poly-4-methylpentenes.

In a fifteenth embodiment, the present disclosure provides a multi-component fiber according to the fourteenth embodiment, wherein the polyolefin comprises polyethylene or polypropylene.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Example 1

A melt-blown (blown microfiber, BMF) nonwoven fiber web was made using Nichigo G-Polymer butanediol vinyl alcohol copolymer (BVOH) pellets (obtained as Nichigo G-Polymer OKS 8112) from the Mitsubishi Chemical Corporation, Tokyo, Japan. A conventional melt-blowing process was employed similar to that described in V. A. Wente, "Superfine Thermoplastic Fibers" in Industrial Engineering Chemistry, Vol. 48, pages 1342 et seq. (1956).

More particularly, the melt-blowing die had circular smooth surfaced orifices, spaced 10 to the centimeter, with a 5:1 length to diameter ratio. Molten (co)polymer was delivered to the die by a 20 mm twin screw extruder commercially available from STEER Co., Union Town, Ohio. This extruder was equipped with two weight loss feeders to control the feeding of the (co)polymer resins to the extruder barrel, and a gear pump to control the (co)polymer melt flow to a die. The extruder temperature was at about 210° C. and it delivered the melt stream to the BMF die, which itself maintained at 210° C. The gear pump was adjusted so that a 0.178 kg/hr/cm die (1.0 lb/hr/inch die width) (co)polymer throughput rate was maintained at the die. The primary air temperature of the air knives adjacent to the die orifices was maintained at approximately 325° C. This produced a web on a rotating collector spaced 18 cm from the die, the speed of the collector was 5 ft/min (1.5 m/min). The web had a basis weight of approximately 100 g/m$^2$, and was composed with the fiber diameter in the range of 5-25 micrometers.

Example 2

A BMF web was made as described in Example 1, except that the speed of the collector speed was reduced to 2.5 ft/min (0.076 m/min). The resultant web had a nominal basis weight of 200 g/m$^2$.

Example 3

BVOH meltblown fibers from Example 1 were fed into a fiber opener and "Roller-Doffed Card" carding machine obtained from Hergeth, Aachen, Germany, forming an unconsolidated mat. The opened BVOH fibers were then blended with opened rayon fiber in a 20:80 weight ratio. The rayon fiber had a fiber diameter of 1.7 decitex (dtex, 10-18 microns) and a length of 39 mm and was obtained as Lenzing Viscose rayon fiber from the Lenzing Group, Lenzing, Austria.

The blended fibers were formed into a web using a conventional air-laying web forming machine (available from the Rando Machine Company, Macedon, New York, under the trade designation RANDO WEBBER), having a nominal basis weight of 200 grams per square meter (gsm). The web was then needletacked resulting in a fiber web having a thickness of 4.2 mm.

Example 4

The nonwoven web was made as described in Example 3, except that melty fibers were added to the composition. The resulting web was a blend of 75 parts by weight (pbw) of rayon, 20 pbw of BVOH fibers and 5 pbw of melty fibers. The melty fibers had a fiber diameter of 4 denier (4.4 decitex, 15-26 microns) and a length of 2 inches (5 cm), and were based on polyester (Tairilin polyester fiber Type LML41, NanYa Plastics Corp., Kaohsiung City, Taiwan).

These web was subjected to heat treatment after the needletacking step to further increase the mechanical properties. The web was placed on a porous belt and sent through a heating apparatus at 300° F. (148° C.) in which hot air was drawn through the thickness of the collected fibers from top to bottom. The resultant fiber web had a nominal basis weight of 200 grams per square meter (gsm). The resulting web had a thickness of 3.9 mm.

Example 5

Multicomponent BMF webs were made using a melt blowing process similar to that described in V. A. Wente, "Superfine Thermoplastic Fibers" in Industrial Engineering Chemistry, Vol. 48, pages 1342 et seq. (1956). The extruder feeding molten (co)polymer to the melt-blowing die was a STEER 20-mm twin screw extruder commercially available from STEER Co., equipped with two weight loss feeders to control the feeding of the (co)polymer resins to the extruder barrel and a melt pump to control the (co)polymer melt flow to a melt-blowing die. The die had a plurality of circular smooth surfaced orifices (10 orifices/cm) with a 5:1 diameter ratio as generally described in are described in, e.g., U.S. Pat. No. 5,232,770 (Joseph et al.).

All of the web examples discussed below were made using an apparatus equipped with a multi-layer feed block configured to obtain multi-component fibers that exhibit an axial cross sectional structure, when the fiber is viewed in axial cross-section, consisting of two layers (side by side). A first BMF web was made with each fiber having 2 side-by-side layers. One layer of the fiber was made of BVOH and the second layer was made using Dow DNDB 1077 Linear low-density polyethylene (LLDPE) from the Dow Chemical Company, Midland, Michigan. The two extruders were kept at the same temperature at 210° C. to deliver the melt stream to the BMF die (maintained at 210° C.). The gear pumps were adjusted to obtain a 50/50 ratio of BVOH/LLDPE with a total polymer throughput rate of 0.178 kg/hr/cm die width (1.0 lb/hr/inch die width) maintained at the BMF die. The primary air temperature was maintained at approximately 325° C. The resulting web was collected at a BMF die to collector distance of 7 inches (18 cm) and a collection rate of 5 ft/min (1.5 m/min). The resultant melt-blown fiber web had a nominal basis weight of 195 g/m². The resulting fibers had fiber diameter in the range of 5 to 30 micrometers.

Example 6

A multicomponent BMF fiber web was made as described in Example 5, except for the following changes: first Layer: 75% BVOH; second Layer: 25% LLDPE. The resulting web was collected at a die to collector distance of 7 inches (18 cm) and a collection rate of 5 ft/min (1.5 m/min). The resultant melt-blown fiber web had a nominal basis weight of 203 g/m². The resulting fibers had fiber diameter in the range of 5 to 30 micrometers.

Example 7

A multicomponent BMF fiber web was made as described in Example 5, except for the following changes:
first Layer: 25% BVOH; second Layer: 75% LLDPE. The resulting web was collected at a die to collector distance of 7 inches (18 cm) and a collection rate of 5 ft/min (1.5 m/min). The resultant melt-blown fiber web had a nominal basis weight of approximately 215 g/m². The resulting fibers had fiber diameter in the range of 5 to 30 micrometers.

All cited references, patents, and patent applications in this application that are incorporated by reference, are incorporated in a consistent manner. In the event of inconsistencies or contradictions between portions of the incorporated references and this application, the information in this application shall control. The preceding description, given in order to enable one of ordinary skill in the art to practice the claimed disclosure, is not to be construed as limiting the scope of the disclosure, which is defined by the claims and all equivalents thereto.

What is claimed is:

1. A method of making a nonwoven fiber web, the method comprising:
    a) providing a melt-blown nonwoven fiber web comprising bonded primary fibers having an average fiber diameter of 2 to 100 microns, wherein the primary fibers comprise a copolymer comprising divalent hydroxyethylene monomer units and divalent dihydroxybutylene monomer units;
    b) opening at least a portion of the melt-blown nonwoven fiber web to provide loose primary fibers;
    c) combining the loose primary fibers with secondary fibers; and
    d) forming a secondary nonwoven fiber web comprising the primary fibers and secondary fibers, wherein said forming the secondary nonwoven fiber web comprises airlaying a fiber blend comprising the loose primary fibers and the secondary fibers.

2. The method of claim 1, wherein the copolymer further comprises divalent acetoxyethylene monomer units.

3. The method of claim 1, wherein the divalent dihydroxybutylene monomer units comprise divalent 3,4-dihydroxybutan-1,2-diyl monomer units.

4. The method of claim 1, wherein the secondary fibers comprise at least one of polyolefin fibers, polyester fibers, polyamide fibers, styrenic block copolymer fibers, polyurethane fibers, metal fibers, ceramic fibers, or natural fibers.

5. A secondary nonwoven fiber web made by the method of claim 1.

* * * * *